United States Patent [19]

Baker et al.

[11] 4,129,594

[45] Dec. 12, 1978

[54] PROCESS FOR THE MANUFACTURE OF AROMATIC DICARBOXYLIC ACID CHLORIDES

[75] Inventors: Josefina T. Baker, Mount Tabor, N.J.; John Pisanchyn, Olyphant, Pa.; Stylianos Sifniades, Madison, N.J.

[73] Assignee: Allied Chemical Corporation, Morris Township, Morris County, N.J.

[21] Appl. No.: 846,098

[22] Filed: Oct. 27, 1977

[51] Int. Cl.$^2$ .................... C07C 63/30; C07C 63/22; C07C 63/38; C07C 63/46

[52] U.S. Cl. .................... 260/544 D; 260/544 B; 260/544 P

[58] Field of Search ............ 260/544 D, 544 B, 544 P

[56] References Cited

FOREIGN PATENT DOCUMENTS 732078 9/1932 France.
1415980 12/1975 United Kingdom .................... 260/544

Primary Examiner—Gerald A. Schwartz
Attorney, Agent, or Firm—Robert J. North; Gerhard H. Fuchs

[57] ABSTRACT

An improved process is described for preparing solutions or slurries of aromatic dicarboxylic acid chlorides in high purity, particularly terephthaloyl chloride, useful as an acylating agent for making polyesters from bisphenols, by adding an aromatic dicarboxylic acid to a liquid medium of phosgene in an inert chlorinated paraffinic hydrocarbon solvent, at a temperature of about 10° to 50° C, wherein at least 1.02 equivalents of a weak tertiary amine base per equivalent of carboxylic acid group is present in the reaction mixture throughout the reaction period, whereby a yield of dicarboxylic acid chloride of at least about 90% of theory, based on the total dicarboxylic acid employed in the reaction, is obtained.

14 Claims, No Drawings

PROCESS FOR THE MANUFACTURE OF AROMATIC DICARBOXYLIC ACID CHLORIDES

BACKGROUND OF THE INVENTION

1. Field of the Invention

This invention relates to an improved process for preparing aromatic dicarboxylic acid chlorides, in high purity in solution or slurry form, by reacting aromatic dicarboxylic acids with phosgene in the presence of a weak tertiary amine base and an inert chlorinated paraffinic hydrocarbon solvent, for direct use as acylating agents.

2. Brief Description of the Prior Art

Aromatic dicarboxylic acid chlorides are well known as acylating agents, particularly, for bisphenols, glycols and diamines in forming aromatic polyesters and polyamides. Optimum conditions for the polymerization usually include the use of aromatic acid chlorides in solution or slurry form for achieving high molecular weight and controlled molecular weight distributions.

Processes for the preparation of carboxylic acid chlorides from the reaction of carboxylic acids with phosgene are known in the art, and are exemplified in the following references.

U.S. Pat. No. 3,869,485 (1975) describes an improved process for the preparation of monocarboxylic acid halides by reaction of monocarboxylic acids or anhydrides with phosgene in the presence of a benzimidazole or benzotriazole catalyst. However, the process requires reaction temperatures above 50° C., preferably from about 100° to 180° C. at atmospheric pressure, during which hydrogen chloride gas is evolved. The high temperatures required, above ambient temperature, adds to the cost of the process and evolution of hydrogen chloride gas at these temperatures may present corrosion problems to the apparatus employed.

British Pat. No. 1,415,980 (1975) describes a process for preparing acid chlorides by reacting carboxylic acids with phosgene at an elevated temperature in the presence of a tertiary amine catalyst. However, the reaction requires elevated temperatures, preferably of about 120° to 160° C., and since an inert organic solvent is not employed, does not result in a solution or slurry of the acid chloride suitable as an acylating agent.

U.S. Pat. No. 3,318,950 (1967) describes a process for preparing carboxylic acid chlorides by reacting intermolecular anhydrides of carboxylic acids with phosgene in the presence of a carboxamide, optionally in the presence of an inert organic solvent. However, the reaction has the disadvantage in that it requires the use of acid anhydrides rather than the acids themselves for the direct production of acid chlorides.

French Pat. No. 732,078 (1932) describes a process for preparing organic acid halides by reacting a carbonyl halide such as phosgene, and an organic acid, in a temperature range including 10°-50° C., and in the presence of an inert organic solvent including chlorinated paraffinic hydrocarbons, using for each acid group of the organic acid, i.e., carboxylic or sulfonic acid group, at most an equivalent amount of a nitrogenous base or salt thereof.

We have unexpectedly found that in preparing aromatic dicarboxylic acid chlorides, in solution or slurry form, from the corresponding dicarboxylic acid by reaction with phosgene at ambient temperatures from about 10° to 50° C., in an inert chlorinated paraffinic hydrocarbon solvent, at least 1.02 equivalents of a weak tertiary amine base per equivalent of carboxylic acid group must be present in the reaction mixture, throughout the reaction period, to obtain the acid chloride in at least about 90% yield of theory, based on the total dicarboxylic acid employed in the reaction. In addition to obtaining high yields of diacid chloride, the process has the advantages of not requiring acid anhydrides as starting materials and allows the production of diacid chlorides from aromatic dicarboxylic acids at ambient temperatures, e.g. 10°-50° C., thus reducing the cost of the process and inhibiting potential corrosion and pollution problems associated with the use of higher temperatures as in the prior art.

SUMMARY OF THE INVENTION

In accordance with this invention, there is provided an improved process for preparing aromatic dicarboxylic acid chlorides, in solution or slurry form for direct use as acylating agents, including adding an aromatic dicarboxylic acid to a liquid medium containing phosgene and a weak tertiary amine base, at a temperature of about 10° to 50° C., in which the improvement comprises providing in the reaction mixture, at least 1.02 equivalents of the weak tertiary amine base per equivalent of carboxylic acid group present in the reaction mixture as such, throughout the reaction period, and providing in the reaction mixture about 8 to 30 parts by weight of an inert chlorinated paraffinic hydrocarbon solvent containing 1-6 carbon atoms and 1-4 chlorine atoms, per part of total dicarboxylic acid employed, whereby a yield of dicarboxylic acid chloride of at least about 90% of theory, based on the total dicarboxylic acid employed in the reaction, is obtained.

DESCRIPTION OF THE INVENTION AND THE PREFERRED EMBODIMENTS

The improved process of this invention is useful in preparing dicarboxylic acid chlorides, in solution or slurry form, for direct use as an acylating medium for a variety of chemical compounds including bisphenols, glycols and diamines. The process is particularly useful for producing solutions or slurries of diacid chlorides for direct acylation of bisphenols to produce aromatic polyesters. The advantage of the present improved process over the prior art is that the solutions or slurries of diacid chlorides can be conveniently prepared, at ambient temperature, by a one-step reaction from the aromatic dicarboxylic acid, in which the percent yield of obtained diacid chloride is at least about 90% of theory. Lower percent yields, as obtained by the prior art, result in substantial amounts of unreacted acid by-product in the mixture, which affects the purity of formed polymers, including polyesters, prepared from the diacid chloride.

Use of less than 1.02 equivalents of base per equivalent of carboxylic acid group in the reaction mixture, throughout reaction period, leads to a yield of diacid chloride in the process lower than the desired 90% yield of theory. It is preferred to use at least about 1.05 equivalents of base and more preferably about 1.1 equivalents of base per carboxylic acid group in the reaction mixture throughout the reaction period, and it is preferred to use not more than 5 equivalents of base and more preferably not more than 2 equivalents of base per equivalent of carboxylic acid group in the total dicarboxylic acid employed, in the reaction mixture throughout the reaction period. Use of more than 5 equivalents of base per equivalent of carboxylic acid group in the total dicarboxylic acid employed, in the reaction mixture throughout the reaction product, leads to inordinately large amounts of base making subsequent recovery and recycle of the base, necessary from economic and pollution control standpoints, a tedious and costly part of an industrial process.

In the process, the weak tertiary amine base may also be added, if desired, with the acid to the liquid medium of phosgene as a solution or slurry with the acid, wherein the base and acid have been reacted to form a salt. Alternately, the base can be present in the medium of phosgene to which the acid is being added.

Weak tertiary amine bases that are useful in the process are those having a $pK_b$ of $9 \pm 2.0$ as measured in aqueous solution at 25° C. Use of a base having a $pK_b$ lower than $9 \pm 2.0$, i.e. a strong base, leads to a yield of diacid chloride in the process less than the desired 90% of theory. The term "tertiary amine" as used herein is well known in the art and refers to organic nitrogen compounds, wherein the nitrogen atoms are connected only to carbon atoms, for example, to linear or branched alkyl of 1 to 18 carbon atoms, e.g. N,N-dimethylaniline. Alternately, the nitrogen atom can be a heterocyclic ring member as in pyridine or quinoline. The term "$pK_b$" as used herein is also a term well known in the art and is the negative logarithm of the term $K_b$, where $K_b = 10^{-14}/K_a$, and $K_a$ is the value, at a particular temperature, of the dissociation constant of the following equilibrium reaction:

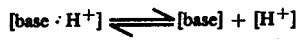

$$K_a = \frac{[base][H^+]}{[base \cdot H^+]}$$

where [base·H$^+$] represents the concentration of the protonated form of the base, [base] represents the concentration of free unprotonated base and [H$^+$] represents the concentration of hydrogen ion, from which the pH can be calculated.

Included among tertiary amine bases that are applicable in the process are pyridine, substituted pyridines, quinoline, substituted quinolines and N,N-disubstituted anilines wherein the substituted pyridines and quinolines may contain inert ring substituents such as halogen, linear or branched alkyl containing 1 to 18 carbon atoms, linear or branched alkoxy containing 1 to 18 carbon atoms, nitro or trifluoromethyl.

Representative examples include pyridine, 2,3- and 4-methylpyridines, quinoline, 2- and 4-methylquinoline, N,N-dimethylaniline, N,N-diethylaniline and the like. A preferred base for use in the process is pyridine.

Aromatic dicarboxylic acids that are useful in the reaction are generally described in the above discussed prior art of French Pat. No. 732,078 and include those containing 8 to 18 carbon atoms. Representative examples of such diacids are terephthalic acid, isophthalic acid, phthalic acid, 1,5- and 2,6-naphthoic acid, 4,4'-benzophenone dicarboxylic acid, phenanthrene dicarboxylic acid, anthracene dicarboxylic acid and the like. A preferred aromatic dicarboxylic acid in the invention process is terephthalic acid.

The term "reaction period" as used herein, refers to the combined times of addition of the acid and the resulting stirring period. Time of addition of the acid to the liquid medium of phosgene is not critical and addition times of about 15 to 30 minutes are usually employed when using laboratory scale quantities. Shorter and longer periods may also be used effectively, especially longer time periods in an industrial process where larger quantities of reactants are employed.

The stirring period, after the acid has been added, is usually about 0.1 to 2 hours. Longer or shorter time periods can also be used with equal effectiveness. It is preferred to allow the reaction mixture to stir for about 0.5 hours after the addition. The resulting solution or slurry of the diacid chloride, after the reaction period, can then be used directly as an acylating medium.

Inert chlorinated paraffinic hydrocarbon solvents useful in the reaction must be liquid, at a temperature between 10° and 50° C., inert under the reaction conditions, and good solvents for the diacid chloride formed in the reaction. In addition, the solvent may be used for forming a slurry of the acid, or alternatively, a slurry of the acid and base for addition to the medium of phosgene. Solvents suitable for use in the process are chlorinated paraffinic hydrocarbons containing 1 to 6 carbon atoms and 1 to 4 chlorine atoms. Representative examples include dichloromethane, 1,2-dichloroethane, symmetrical tetrachloroethane, chloroform and the like. Particularly preferred is dichloromethane.

The solvent is generally used in a ratio of about 8 to 30 parts by weight per part of acid and smaller or larger amounts of solvent can also be used with success. A preferred range is about 10 to 20 parts of solvent by weight per part of acid.

The percent yield of diacid chloride from the reaction of phosgene with aromatic dicarboxylic acid is at least about 90% of theory based on the total acid employed in the reaction and preferably a yield of 97% and higher is generally achieved in the process.

The temperature of the process is generally conducted and maintained in the range from about 10° to about 50° C, as described in the prior art and the preferred temperature range generally used is from about 15° to 30° C.

The amount of phosgene that is used is generally about 1 equivalent per equivalent of acid as described in the prior art of U.S. Pat. No. 3,547,960, and it is preferred to use a slight excess in an amount of about 1.02 to 1.05 moles phosgene per equivalent of acid to insure complete conversion of the acid to the acid chloride. The phosgene may be charged into the liquid organic reaction medium either as a gas or a liquid, and the amount delivered is determined by the increase in the weight of liquid reaction medium, as is conventional in the art. After charging the phosgene, the mixture temperature is adjusted to 10°–50° C. prior to the addition of the acid. At the end of the reaction, the excess phosgene can be removed from the reaction medium, as for example, by purging the reaction medium with dry nitrogen.

The invention process can be conducted in the open or closed to the atmosphere, but it is preferred to conduct the reaction in a dry atmosphere protected from atmospheric moisture to preclude any hydrolysis of formed acid chloride or reaction of moisture with the phosgene reagent.

The process of the present invention may also be carried out in a continuous manner by simultaneously adding to a reactor, an inert chlorinated paraffinic hydrocarbon solvent, a weak tertiary amine, an aromatic dicarboxylic acid and phosgene, provided that the respective ratios of the reagents and the solvent are maintained within the limits specified in the foregoing, namely, 8 to 30 parts by weight of solvent per part of diacid, at least 1.02 equivalents of weak base per carboxylic acid group and at least 1.02 moles of phosgene per carboxylic acid group.

A preferred embodiment of the process is where terephthalic acid is added to a dichloromethane medium containing phosgene and pyridine, wherein the pyridine is present in an amount of about 1.1 equivalents per equivalent of carboxylic acid group as such, and not more than about 2 equivalents per equivalent of carboxylic acid group in the total terephthalic acid employed, in the reaction mixture throughout the reaction period, and the dichloromethane is present in an amount of about 10 to 20 parts by weight per part of total terephthalic acid employed at a temperature of about 15° to 30° C., whereby a yield of terephthaloyl chloride of at least about 97% theory, based on the total terephthalic acid employed in the reaction, is obtained.

The solution or slurry of diacid chloride formed from the reaction process can be used to directly acylate a wide variety of reagents such as mono- and difunctional amines, alcohols and phenols.

A particularly preferred class of reagents that can be directly acylated by the solution or slurry of diacid chloride are the bisphenols containing 12–17 carbon atoms. In general, the bisphenols can be directly added to the solution or slurry of diacid chloride and reacted at ambient temperature to form aromatic polyesters. Representative examples of bisphenols include 2,2-bis(4'-hydroxyphenyl)propane, 4,4'-dihydroxybiphenyl, 2,2-bis(4'-hydroxy-3'-methylphenyl)propane, bis(4'-hydroxyphenyl)dichloromethane and the like. A preferred bisphenol for this reaction is 2,2-bis(4'-hydroxyphenyl)propane. Polyesters formed from the reaction can then be further reacted with reagents, for example, phosgene, to form high molecular weight polyester-carbonates.

A preferred embodiment of this invention process is wherein the final mixture containing the diacid chloride reaction product, dichloromethane and pyridine hydrochloride is added to a mixture of 2,2-bis(4'-hydroxyphenyl)propane, dichloromethane, and pyridine to produce low molecular weight 2,2-bis(4'-hydroxyphenyl)-propane/terephthalic acid polyester.

Alternately, a monofunctional reagent such as methanol can be used to react with the solution or slurry of diacid chloride to form aromatic esters, e.g. dimethyl terephthalate, which in turn can be directly reacted with diamines, such as hexamethylene diamine to form aromatic polyamides.

Other reagents which can be acylated with the solution or slurry of diacid chloride will be obvious to one skilled in the art.

The solution or slurry of diacid chloride after preparation can also be stored indefinitely and protected from atmospheric moisture and can then be utilized in much the same manner as a shelf reagent.

It is to be understood that the scope of the invention covers not only those variations or modifications of the process which have been specifically disclosed, but also those modifications which would be obvious to one skilled in the art.

The following examples are illustrative of our invention and set forth the best mode which we have contemplated of carrying out the invention, but should not be construed to be limitations on the scope or spirit of the invention. Parts are by weight unless otherwise indicated.

EXAMPLE 1

Into a reaction vessel was charged 280 parts of dry dichloromethane (DCM) and 13.20 parts of dry pyridine. The contents were stirred at room temperature, from 20° to 30° C., and 15.95 parts of phosgene were added to the stirred solution resulting in a faintly yellow solution. Terephthalic acid, 13.23 parts, were then added over about a 1 hour period from an attached addition tube protected from atmospheric moisture. The ratio of equivalents of pyridine base/COOH acid group was 1.05. A gentle evolution of carbon dioxide was observed while the acid was being added. After the addition of acid was complete the contents were allowed to stir at room temperature for about 30 minutes. Excess phosgene was then purged out by bubbling dry nitrogen gas at about 35° to 40° C. through the reaction mixture for about 1.5 hours.

To determine the yield of acid chloride without isolation, the acid chloride was esterified by adding a mixture of about 48 parts anhydrous methanol and about 30 parts dry pyridine to the acid chloride solution at about 40° C. with cooling. The resulting mixture was stirred at ambient temperature for about 1.5 hours. Dilute hydrochloric acid, 3 Normal, was added to neutralize the excess pyridine, dichloromethane and methanol were distilled off under vacuum. The aqueous slurry was diluted with ice and water, the slurry filtered and the precipitate thoroughly washed with water and dried at 40° C. under vacuum. Analysis of the solid by infrared spectroscopy and nuclear magnetic resonance spectroscopy, confirmed the structure as being dimethyl terephthalate, and quantitative analysis by gas chromatography versus standards showed the yield of the esterification product, dimethyl terephthalate, as being 100% of theory, corresponding to a quantitative yield of terephthaloyl chloride formed initially in the reaction.

EXAMPLE 2 (Comparison)

Following the general procedure of Example 1, for preparation of the diacid chloride, 10.12 parts of terephthalic acid were added to a mixture of 7.93 parts pyridine and 13.63 parts phosgene in 280 parts dry dichloromethane at 25° to 30° C. The ratio of equivalents of pyridine base/COOH acid group was 0.82. After carrying out the reaction and esterifying the resulting diacid chloride by the procedure described in Example 1, 11.39 parts of solids were obtained. Analysis of the product composition by gas chromotography showed that 72.5 weight percent of the composition was dimethyl terephthalate along with 6.2 weight percent of unreacted terephthalic acid. This corresponds to a yield of 69.8% percent of theory of terephthalolyl chloride formed initially in the reaction.

EXAMPLE 3

Following the general procedure of Example 1 for preparation of the diacid chloride, 9.85 parts of terephthalic acid were added to a mixture of 11.52 parts pyridine and 13.2 parts phosgene in 200 parts dry dichloromethane at 25° to 30° C. The ratio of equivalents of pyridine base/COOH acid group was 1.23. After carrying out the reaction to produce diacid chloride and purging out excess phosgene, the diacid chloride was isolated from the solution by acidifying the solution with anhydrous hydrogen chloride, adding 800 parts dry carbon tetrachloride, filtering off formed pyridine hydrochloride, washing the precipitate with 2–150 part portions of carbon tetrachloride, combining the carbon tetrachloride filtrates, and distilling the carbon tetrachloride under vacuum at 35° to 40° C. to yield solid terephthaloyl chloride residue in 99% yield of theory and of 93.2% purity as determined by gas chromatographic analysis. The impurity is believed to be pyridine hydrochloride.

EXAMPLE 4

Following the general procedure of Example 1 for preparation of the diacid chloride, 10.46 parts of terephthalic acid were added to a mixture of 11.6 parts pyridine and 14.6 parts phosgene in 200 parts dry dichloromethane at 25° to 30° C. The ratio of equivalents of pyridine base/COOH acid group was 1.16. After reaction to produce acid chloride and driving off excess phosgene, the acid chloride was isolated from the solution by acidifying the final solution with anhydrous hydrogen chloride and then distilling off dichloromethane under vacuum at about 35° C. The resulting residue was reslurried in 800 parts carbon tetrachloride, filtered to remove precipitated pyridine hydrochloride, and the precipitate washed twice with 150 part portions of carbon tetrachloride. The combined carbon tetrachloride filtrate and washings were then distilled at 35° to 40° C. under vacuum to remove carbon tetrachloride. The resulting residue was terephthaloyl chloride obtained in 97.3% yield of theory and 100% purity as determined by gas chromatographic analysis.

EXAMPLE 5 (Comparison)

This example illustrates that a strong tertiary amine base is not applicable in the invention process for producing acid chlorides.

Following the general procedure in Example 1 for the preparation of the diacid chloride, 10.13 parts of terephthalic acid were added to a mixture of 14.7 parts triethylamine and 14.4 parts phosgene in 200 parts dry dichloromethane at 25° to 30° C. The ratio of equivalents of triethylamine base/COOH acid group was 1.19. After carrying out the reaction and esterifying the resulting diacid chloride by the procedure described in Example 1, no dimethyl terephthalate was isolated. Instead, 100% recovery of unreacted terephthalic acid was obtained.

EXAMPLE 6

Following the general procedure in Example 1 for the preparation of the diacid chloride, 8.93 parts of terephthalic acid were added to a mixture of 16.47 parts of N,N-dimethyl aniline and 12.8 parts phosgene in 200 parts dry dichloromethane at 25° to 30° C. The ratio of equivalents of dimethylaniline base/COOH acid group was 1.26. After carrying out the reaction and esterifying the resulting diacid chloride by the procedure described in Example 1, 9.87 parts of a solid containing 95.4% dimethyl terephthalate was obtained corresponding to a 90.2% yield of theory of terephthaloyl chloride formed initially in the reaction.

EXAMPLE 7

Following the general procedure of Example 1 for the preparation of the diacid chloride, 9.06 parts of terephthalic acid were added to a mixture of 11.82 parts of 4-methylpyridine and 14.1 parts phosgene in 200 parts dry dichloromethane at 25° to 30° C. The ratio of equivalents of methylpyridine base/COOH acid group was 1.16. After carrying out the reaction and esterifying the resulting diacid chloride by the procedure described in Example 1, a 100% yield of dimethyl terephthalate was obtained corresponding to a quantitive yield of terephthaloyl chloride formed initially in the reaction.

EXAMPLE 8

This example illustrates the use of another chlorinated paraffinic hydrocarbon solvent.

Following the general procedure of Example 1 for the preparation of the diacid chloride, 10.31 parts of terephthalic acid were added to a mixture of 10.57 parts pyridine and 14.5 parts phosgene in 200 parts dry 1,2-dichloroethane at 25° to 30° C. The ratio of equivalents of pyridine base/COOH acid group was 1.08. After carrying out the reaction and esterifying the resulting diacid chloride by the procedure described in Example 1, a 95% yield of theory of dimethyl terephthalate was obtained corresponding to a 95% yield of theory of terephthaloyl chloride formed initially in the reaction.

EXAMPLE 9 (Comparison)

This example illustrates the use of a slurry of the diacid in the addition as contrasted to the addition of solid diacid in the procedure of Example 1. Also, the ratio of equivalents of base/COOH group used was below 1.02 resulting in a yield of the diacid chloride lower than 90 percent of theory.

Into a suitable reaction vessel, 260 parts dry dichloromethane and 8.14 parts dry pyridine were charged. The mixture was stirred and to this was added 14 parts phosgene with cooling at about 5° C. The resulting cloudy mixture was allowed to warm to about 24° C. A slurry of 10.69 parts terephthalic acid in 100 parts dry dichloromethane was added over about a 30 minute period. During the addition, the temperature rose from 24° to 30° C. and a vigorous evolution of carbon dioxide was observed. The ratio of equivalents of pyridine base/COOH acid group was 0.80. The mixture was stirred after the addition for 2 hours at 24° to 30° C. The reaction mixture was treated by the esterification procedure described in Example 1 resulting in a 70.2% yield of theory of dimethyl terephthalate corresponding to a 70.2% theory of terephthaloyl chloride formed initially in the reaction. Also recovered was 8.8 weight percent of the starting diacid.

EXAMPLE 10

Following the general procedure of Example 9, a slurry of 8.28 parts terephthalic acid in 80 parts dry dichloromethane was added to a stirred mixture of 8.72 parts pyridine and 10.84 parts phosgene in 210 parts dry dichloromethane at 24° to 30° C. The ratio of equivalents of pyridine base/COOH acid groups was 1.10. After carrying out the reaction and esterifying the resulting diacid chloride by the procedure described in Example 1, there was obtained a 100% yield of dimethyl terephthalate, corresponding to a 100% yield of terephthaloyl chloride, formed initially in the reaction.

EXAMPLE 11

Following the general procedure of Example 9, a slurry of 7.46 parts isophthalic acid in 80 parts dry dichloromethane was added to a mixture of 7.91 parts pyridine and 9.77 parts phosgene in 210 parts dry dichloromethane at 25° to 30° C. The ratio of equivalents of pyridine base/COOH acid group was 1.10. After carrying out the reaction and esterifying the resulting diacid chloride by the procedure described in Example 1 there was obtained a 100% yield of dimethyl isophthalate corresponding to a 100% yield of isophthaloyl chloride formed initially in the reaction.

EXAMPLE 12

Following the general procedure of Example 9, a slurry of 7.13 parts terephthalic acid in 80 parts dry dichloromethane was added to a mixture of 6.93 parts pyridine and 9.35 parts phosgene in 210 parts dry dichloromethane at 25° to 30° C. The ratio of equivalents of pyridine base/COOH acid group was 1.02. After carrying out the reaction and esterifying the resulting diacid chloride by the procedure as described in Example 1, there was obtained a 94.2% yield of theory of dimethyl terephthalate corresponding to a 94.2% yield of terephthaloyl chloride formed initially in the reaction.

EXAMPLE 13

Following the general procedure of Example 9, but using more concentrated reaction media, a slurry of 8.22 parts terephthalic acid in 50 parts dry dichloromethane was added to a stirred mixture of 8.85 parts pyridine and 10.46 parts phosgene in 80 parts dry dichloromethane at 24° to 30° C. The ratio of equivalents of pyridine base/COOH acid group was 1.13. After carrying out the reaction and esterifying the resulting diacid chloride by the procedure as described in Example 1, a quantitative yield of dimethyl terephthalate was formed corresponding to a quantitative yield of terephthaloyl chloride formed initially in the reaction.

EXAMPLE 14 (Comparison)

This example illustrates that conducting the reaction in the absence of an inert organic solvent at room temperature results in a yield of diacid chloride lower than 90% of theory despite the fact that a large amount of weak tertiary amine base was used.

Phosgene, 3.54 parts, was charged to 150 parts of pyridine at room temperature forming a thick, yellow slurry. To the resulting slurry was added a solution of 2.36 parts of terephthalic acid in about 30 parts pyridine from an addition funnel over a 15 minute period at about 24°–28° C. The addition funnel was further rinsed with about 10 parts pyridine and this was added to the reaction mixture. The ratio of equivalents of pyridine base/COOH group was 84.5. The resulting greenish slurry was stirred for 2 hours at 24°–28° C. Methanol, 40 parts, was then added, while cooling the reaction mixture between 24°–32° C., to esterify formed diacid chloride. The mixture was then stirred for 1.5 hours. The product was then diluted with ice-water and acidified with dilute hydrochloric acid. The formed solids were collected by filtration, thoroughly washed with water, and dried under vacuum at 40° C. overnight. Obtained was 1.8 g. of white powder, melting point 136°–230° C. Analysis of the powder by gas chromatography, and taking the total mass balance into account in light of some mechanical losses, showed that a maximum yield of 86% of theory of terephthaloyl chloride had been formed.

EXAMPLE 15

Following the general procedure of Example 9, a slurry of terephthaloyl chloride was prepared by adding a slurry of 8 parts terephthalic acid and 80 parts dichloromethane to a stirred mixture of 8.74 parts pyridine and 10 parts phosgene in 200 parts dry dichloromethane at 25° to 30° C. The ratio of equivalents of pyridine base/COOH acid group was 1.15. The mixture was stirred for 2 hours at 24° to 30° C. to convert the diacid to the diacid chloride. Analysis of a duplicate run indicated a quantitive yield of terephthaloyl chloride was formed. The above mixture of terephthaloyl chloride was added to a solution of 21.98 parts 2,2-bis(4'-hydroxyphenyl)propane and 23.7 parts pyridine in 135 parts dry dichloromethane over about 30 minutes at 24° to 30° C. An additional 54 parts of dichloromethane was used to rinse the addition funnel containing a small amount of terephthaloyl chloride and was added to the resulting mixture and the mixture stirred for about 0.5 hours at 24° to 30° C. Analysis of the resulting mixture by high pressure liquid chromatography showed that the qualitative and quantitative mixture of oligomer products formed were of the following formula:

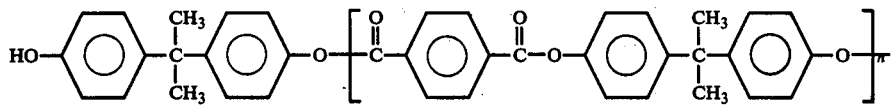

where $n$ is an integer from 1 to 5, and was about the same as an oligomer product mixture derived from polymer grade terephthaloyl chloride of 100% purity. Analysis by gas chromatography did not detect the presence of free terephthalic acid.

EXAMPLE 16

To the resulting oligomer solution formed in Example 15, was added 4.3 parts phosgene at 24°–30° C. over about a 30 minute period. The resulting mixture was poured into 800 parts acetone under brisk agitation. Dichloromethane was distilled off under vacuum and the resulting slurry was further diluted with water. The resulting slurry was filtered and the precipitated solid thoroughly washed with water and dried at 70° C. for about 24 hours yielding 29 parts of white polyester-carbonate. Analysis of the polyester-carbonate showed no free terephthalic acid present and the properties of the polymer were very similar to polyester-carbonate prepared from polymer grade terephthaloyl chloride-2,2-bis(4'-hydroxyphenyl)propane oligomer and phosgene.

We claim:

1. In a process for preparing aromatic dicarboxylic acid chlorides, in solution or slurry form for direct use as acylating agents, which comprises adding an aromatic dicarboxylic acid to a liquid medium containing phosgene and a weak tertiary amine base at a temperature of about 10° to 50° C., the improvement which comprises providing in the reaction mixture, at least 1.02 equivalents of the weak tertiary amine base having a $pK_b$ of 9.0 ± 2.0 as measured in aqueous solution at 25° C. per equivalent of carboxylic acid group present in the reaction mixture as such, throughout the reaction period, and providing in the reaction mixture about 8 to 30 parts by weight of a chlorinated paraffinic hydrocarbon solvent containing 1-6 carbon atoms and 1-4 chlorine atoms per part of total dicarboxylic acid employed, whereby a yield of dicarboxylic acid chloride of at least about 90% of theory, based on the total dicarboxylic acid employed in the reaction, is obtained.

2. The process of claim 1 wherein at least about 1.05 equivalents of said base per equivalent of carboxylic acid group, present in the reaction mixture as such, and not more than about 5 equivalents of said base per equivalent of carboxylic acid group in the total dicarboxylic acid employed, is present in the reaction mixture throughout the reaction period.

3. The process of claim 2 wherein about 1.1 equivalents of said base per equivalent of carboxylic acid group present in the reaction mixture as such, and not more than about 2 equivalents of said base per equivalent of carboxylic acid group in the total dicarboxylic acid employed, is present in the reaction mixture throughout the reaction period.

4. The process of claim 1 wherein the reaction is conducted in the presence of 10 to 20 parts of said inert solvent per part of total dicarboxylic acid employed.

5. The process of claim 1 wherein the weak tertiary amine base is pyridine.

6. The process of claim 1 wherein the inert solvent is dichloromethane.

7. The process of claim 1 whereby the dicarboxylic acid chloride is obtained in a yield of at least about 97% of theory based on the total dicarboxylic acid employed.

8. The process of claim 1 wherein the aromatic dicarboxylic acid contains 8 to 18 carbon atoms.

9. The process of claim 8 wherein the aromatic dicarboxylic acid is terephthalic acid.

10. The process of claim 1 wherein the reaction is conducted in the temperature range of 15° to 30° C.

11. The process of claim 1 wherein the weak tertiary amine base is added with the acid to the phosgene medium.

12. The process of claim 1 wherein the aromatic dicarboxylic acid is added to the liquid medium containing phosgene and weak tertiary amine base.

13. The process of claim 1 wherein the final mixture containing the acid chloride reaction product, dichloromethane and pyridine hydrochloride is added to 2,2'-bis(4'-hydroxyphenyl)propane, dichloromethane, and pyridine to produce low molecular weight 2,2-bis(4'-hydroxyphenyl)propane/terephthalic acid polyester.

14. The process of claim 1 wherein terephthalic acid is added to a dichloromethane medium containing phosgene and pyridine, wherein the pyridine is present in an amount of about 1.1 equivalents per equivalent of carboxylic acid group as such, and not more than about 2 equivalents per equivalent of carboxylic acid group in the total terephthalic acid employed, in the reaction mixture throughout the reaction period, and the dichloromethane is present in an amount of about 10 to 20 parts by weight per part of total terephthalic acid employed, at a temperature of about 15° to 30° C., whereby a yield of terephthaloyl chloride of at least about 97% of theory, based on the total terephthalic acid employed in the reaction, is obtained.

* * * * *